(12) United States Patent
Akai et al.

(10) Patent No.: US 9,290,795 B2
(45) Date of Patent: Mar. 22, 2016

(54) NUCLEIC ACID AMPLIFICATION APPARATUS AND METHOD

(75) Inventors: Yasumasa Akai, Ono (JP); Kadzuki Nakabayashi, Hirakata (JP); Eiji Tanoshima, Kobe (JP)

(73) Assignee: Sysmex Corporation, Kobe (JP)

( * ) Notice: Subject to any disclaimer, the term of this patent is extended or adjusted under 35 U.S.C. 154(b) by 518 days.

(21) Appl. No.: 11/698,137

(22) Filed: Jan. 26, 2007

(65) Prior Publication Data

US 2007/0178513 A1 Aug. 2, 2007

(30) Foreign Application Priority Data

Jan. 27, 2006 (JP) .................................. 2006-18371

(51) Int. Cl.
| | |
|---|---|
| G06F 19/00 | (2011.01) |
| B01L 7/00 | (2006.01) |
| C12Q 1/68 | (2006.01) |
| C12M 3/00 | (2006.01) |
| G01N 35/00 | (2006.01) |

(52) U.S. Cl.
CPC .............. *C12Q 1/6806* (2013.01); *C12M 3/00* (2013.01); *C12Q 1/6848* (2013.01); *G01N 35/0099* (2013.01); *B01L 7/52* (2013.01)

(58) Field of Classification Search
None
See application file for complete search history.

(56) References Cited

U.S. PATENT DOCUMENTS

| | | | |
|---|---|---|---|
| 2004/0053290 A1* | 3/2004 | Terbrueggen et al. ............. | 435/6 |
| 2005/0042138 A1 | 2/2005 | Ueda et al. | |
| 2006/0188911 A1 | 8/2006 | Otomo et al. | |

FOREIGN PATENT DOCUMENTS

| | | |
|---|---|---|
| EP | 0 563 893 A2 | 10/1993 |
| EP | 0 676 643 A2 | 10/1995 |
| EP | 0 681 184 A1 | 11/1995 |
| EP | 1 508 809 A1 | 2/2005 |
| JP | 2004-203 A | 1/2004 |

OTHER PUBLICATIONS

Suslov et al. PCR inhibition by reverse transcriptase leads to an overestimation of amplification efficiency. Nucleic Acids Res. (2005) vol. 33, No. 20, e181, pp. 1-12.*
Stahlberg, A. et al, "Quantitative real-time PCR method for detection of B-lymphocyte monoclonality by comparison of kappa and lambda immunoglobulin light chain expression", Clinical Chemistry, American Association for Clinical Chemistry, Washington, DC, US, vol. 49, No. 1, Jan. 2003, pp. 51-59, XP002392048.
Dumonceaux, et al, "Enumeration of specific bacterial populations in complex intestinal communities using quantitative PCR based on the chaperonin-60 target", Journal of Microbiological Methods, Elsevier, Amsterdam, NL, vol. 64, No. 1, Aug. 19, 2005, pp. 46-62, XP005212482.
Ramakers, C, et al, "Assumption-free analysis of quantitative real-time polymerase chain reaction (PCR) data", Neuroscience Letters, Limerick, IE, vol. 339, No. 1, Mar. 13, 2003, pp. 62-66, XP002330743.

* cited by examiner

*Primary Examiner* — Kenneth R. Horlick
*Assistant Examiner* — David Thomas
(74) *Attorney, Agent, or Firm* — Sughrue Mion, PLLC (57) ABSTRACT

A nucleic acid amplification apparatus for amplifying a target nucleic acid derived from living organism, comprising: a measurement unit for amplifying the target nucleic acid in a measuring sample prepared from the living organism, and measuring a product of the amplification of the target nucleic acid; a measurement value obtaining unit for obtaining a measurement value related to an amount of the product of the amplification; and a judging unit for judging whether amplification inhibition of the target nucleic acid occur or not based on a first measurement value and a second measurement value, the first measurement value obtained from a first measurement sample and the second measurement value obtained from a second measurement sample having a difference dilution ratio from the first measurement sample.

19 Claims, 9 Drawing Sheets

| Sample specimen (CK19) \ Dilution sample (CK19-D) | copy<250 | 250≦copy |
|---|---|---|
| 250≦copy | (+) | (+) |
| copy<250 | (−) | (+) I |

NUCLEIC ACID AMPLIFICATION APPARATUS AND METHOD

FIELD OF THE INVENTION

The present invention relates to a nucleic acid amplification apparatus and method and more particularly, to a nucleic acid amplification and method capable of amplifying and measuring a target nucleic acid in a sample derived from living organism.

BACKGROUND

In recent years, gene testing has been becoming rapidly widely used in the clinical diagnosis field. With gene testing, nucleic acids and chromosomes are analyzed to allow for examination of presence or absence of variations and nuclear forms associated with hereditary disorders for clinical purposes. As one example of gene testing, diagnosis of cancer cell metastasis to lymph nodes is mentioned. Cancer cells leave primary tumor and spread by metastasis all over patient's body via blood vessels and lymph ducts. At operation of a cancer, lesions should be removed as much surely as possible, and therefore, metastasis should be detected accurately and appropriate treatments be provided depending on the degree of metastasis. In this sense, diagnosis of cancer cell metastasis to lymph nodes made during the operation has an extremely important meaning. As one of methods of diagnosis of cancer cell metastasis to lymph nodes, such a method is known that nucleic acid of a protein, that is not expressed in normal cells or expression level thereof is low but is expressed a great deal in cancer cells, is detected as a target nucleic acid. Thanks to advancement of gene analysis technology made in these years, it is now possible to perform cancer diagnosis effectively by detecting a target nucleic acid contained in the lymph node tissue resected from the living organism through amplification.

As mentioned above, when it is desired to make judgment of cancer cell metastasis to lymph nodes by amplification of target nucleic acid, amplification of target nucleic acids in a measurement sample is performed using a measurement sample which is prepared in such that lymph nodes are homogenized and target nucleic acids are extracted into a solution and purified. However, with this method, there is such a drawback that purification of the target nucleic acid needs considerable time, it takes longer time before results of the judgment by amplification of the target nucleic acid are made available, and it is difficult to perform promptly diagnosis of cancer cell metastasis by amplification of the target nucleic acid. At diagnosis of cancer cell metastasis to lymph nodes during the operation, treatment strategy in the operation is determined according to results of judgment of metastasis of cancer cells, and therefore, quick judgment of metastasis is so important.

From viewpoints mentioned above, if a solution in which lymph nodes are homogenized or supernatant of this solution is used as the measurement sample without executing extraction and purification of the nucleic acid at the time of preparation of measurement sample, it is possible to perform measurements of the target nucleic acid in prompt fashion. However, when the target nucleic acid is amplified using such a measurement sample, there is such a problem that, compared to a case where amplification of nucleic acids is made using a measurement sample prepared by purification of the nucleic acid, the amount of inhibitory substances that prevent amplification of the target nucleic acid derived from lymph nodes increases and accurate measurement results can not be thus obtained.

In order to overcome this problem, conventionally, such a method is known that amplification of a target nucleic acid is estimated using a nucleic acid probe which hybridizes to the target nucleic acid (see, for example, Japanese Patent Application Laid-Open No. 2004-203). According to the method disclosed in Japanese Patent Application Laid-Open No. 2004-203, a nucleic acid (internal standard nucleic acid) in which base sequence of the target nucleic acid is mutated in part is added to a measuring system at known concentration, and at the same time, a target nucleic acid probe that hybridizes specifically to the target nucleic acid and an internal standard nucleic acid probe that hybridizes specifically to the internal standard nucleic acid are added to the measuring system, the target nucleic acid and the internal standard nucleic acid are then measured at one time using PCR method, and the target nucleic acid is measured from an amount of addition of the internal standard nucleic acid.

However, with the method for measuring the target nucleic acid disclosed in above-mentioned Japanese Patent Application Laid-Open No. 2004-203, the internal standard nucleic acid does not necessarily exhibit the same reactivity as the target nucleic acid does, and therefore, a problem arises that accurate measurement of the target nucleic acid is difficult.

SUMMARY

The scope of the present invention is defined solely by the appended claims, and is not affected by any degree by the statements within this summary.

A nucleic acid amplification apparatus according to a first aspect of the present invention is a nucleic acid amplification apparatus for amplifying a target nucleic acid derived from living organism, comprising: a measurement unit for amplifying the target nucleic acid in a measuring sample prepared from the living organism, and measuring a product of the amplification of the target nucleic acid; a measurement value obtaining unit for obtaining a measurement value related to an amount of the product of the amplification; and a judging unit for judging whether amplification inhibition of the target nucleic acid occur or not based on a first measurement value and a second measurement value, the first measurement value obtained from a first measurement sample and the second measurement value obtained from a second measurement sample having a difference dilution ratio from the first measurement sample.

A nucleic acid amplification method according to a second aspect of the present invention is a nucleic acid amplification method for amplifying a target nucleic acid derived from living organism, comprising steps of: amplifying the target nucleic acid in a first measuring sample prepared from the living organism; amplifying the target nucleic acid in a second measuring sample prepared from the living organism and had a difference dilution ratio from the first measurement sample; measuring a first product of the amplification of the target nucleic acid of the first measurement sample; measuring a second product of the amplification of the target nucleic acid of the second measurement sample; obtaining a first measurement value related to an amount of the first product of the amplification; obtaining a second measurement value related to an amount of the second product of the amplification; and judging whether amplification inhibition of the target nucleic acid occur or not based on the first measurement value and the second measurement value.

BRIEF DESCRIPTION OF THE DRAWINGS

FIG. 1 is a plan view showing whole composition of an immune analysis apparatus equipped with a pipette chip supplying apparatus by one embodiment according to the present invention.

DETAILED DESCRIPTION OF THE PREFERRED EMBODIMENT

Now, embodiments of the present invention will be explained hereinafter referring to the drawings.

A gene amplification and analysis system 1 according to the present embodiment is a system supporting cancer metastasis diagnosis for resected tissue (lymph node) at operation of cancer, wherein target gene (mRNA) originated from cancer existing in the resected tissue is amplified by LAMP (Loop-Medicated Isothermal Amplification, Eiken Chemical Co., Ltd.) method, and white turbidity due to magnesium pyrophosphate, which is generated by amplification, is measured by turbidimetry to know whether or not the target gene is present at a predetermined level or more. Meanwhile, details of the LAMP method are disclosed in U.S. Pat. No. 6,410,278.

Figure 1:
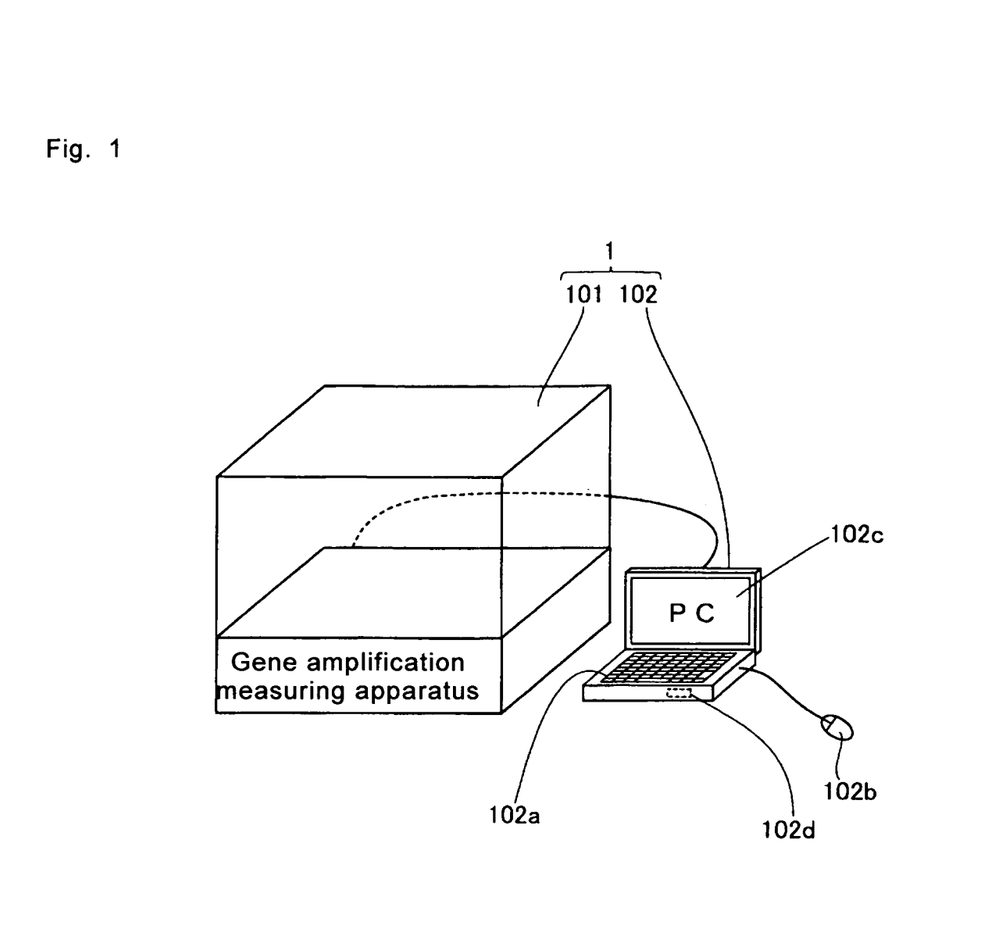
FIG. 1 is a perspective illustration showing whole composition of a gene amplification and analysis system by one embodiment according to the present invention.

The gene amplification and analysis system 1 of the present embodiment comprises, as shown in FIG. 1, a gene amplification measuring apparatus 101 and a personal computer (PC) 102 connected so as to allow communication with the gene amplification measuring apparatus 101 in wired or wireless fashion.

First, referring to FIGS. 1 to 3, details of the gene amplification measuring apparatus 101 will be explained. The gene amplification measuring apparatus 101 includes, as shown in FIGS. 2 and 3, a dispensing mechanism 10, a sample specimen setting unit 20, a chip setting unit 30, a chip disposal unit 40, and a reaction detection unit 50 comprising five reaction detection blocks 50a, and a transfer unit 60 for transferring the dispensing mechanism 10 in X-axis direction and Y-axis direction.

Figure 2:
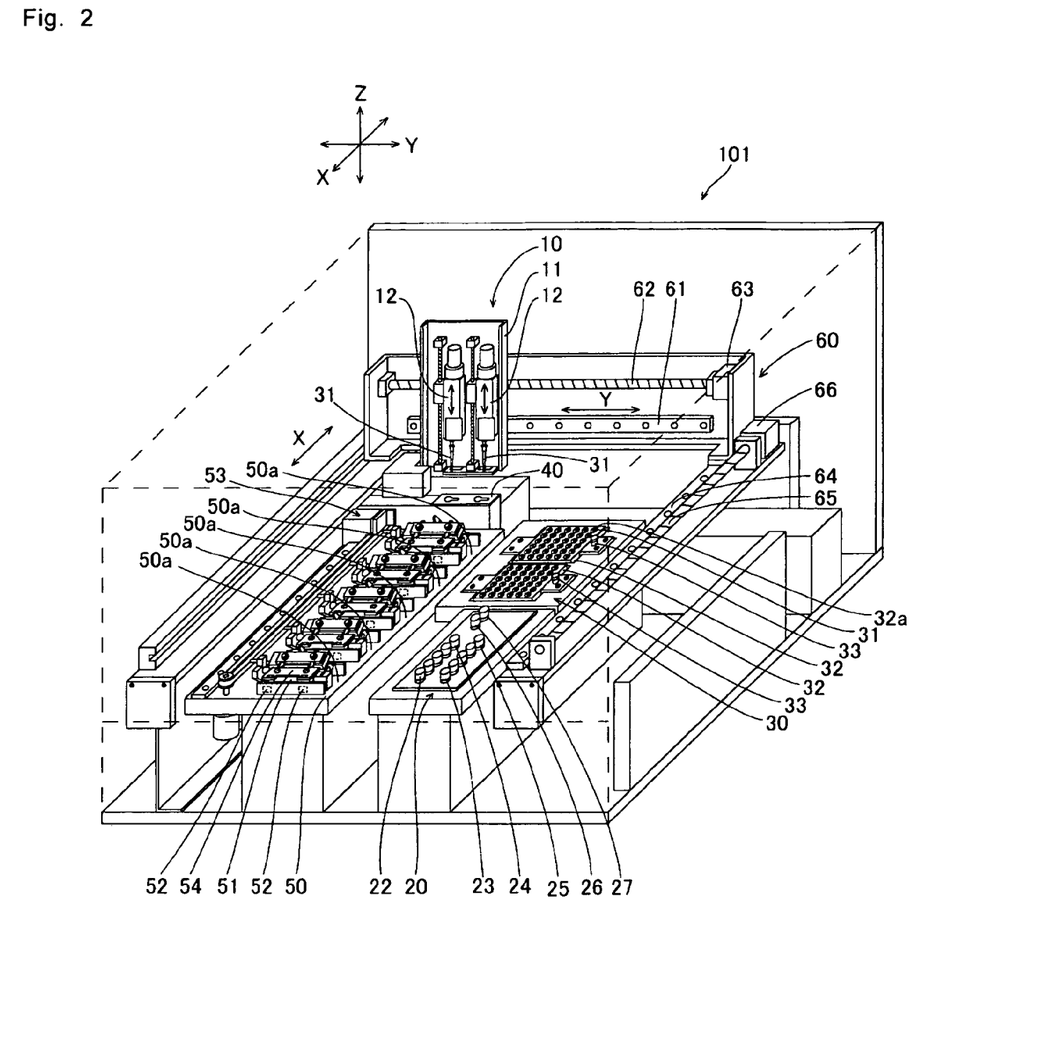
FIG. 2 is a perspective illustration showing whole composition of a gene amplification measuring apparatus of the gene amplification and analysis system by one embodiment shown in FIG. 1.
Figure 3:
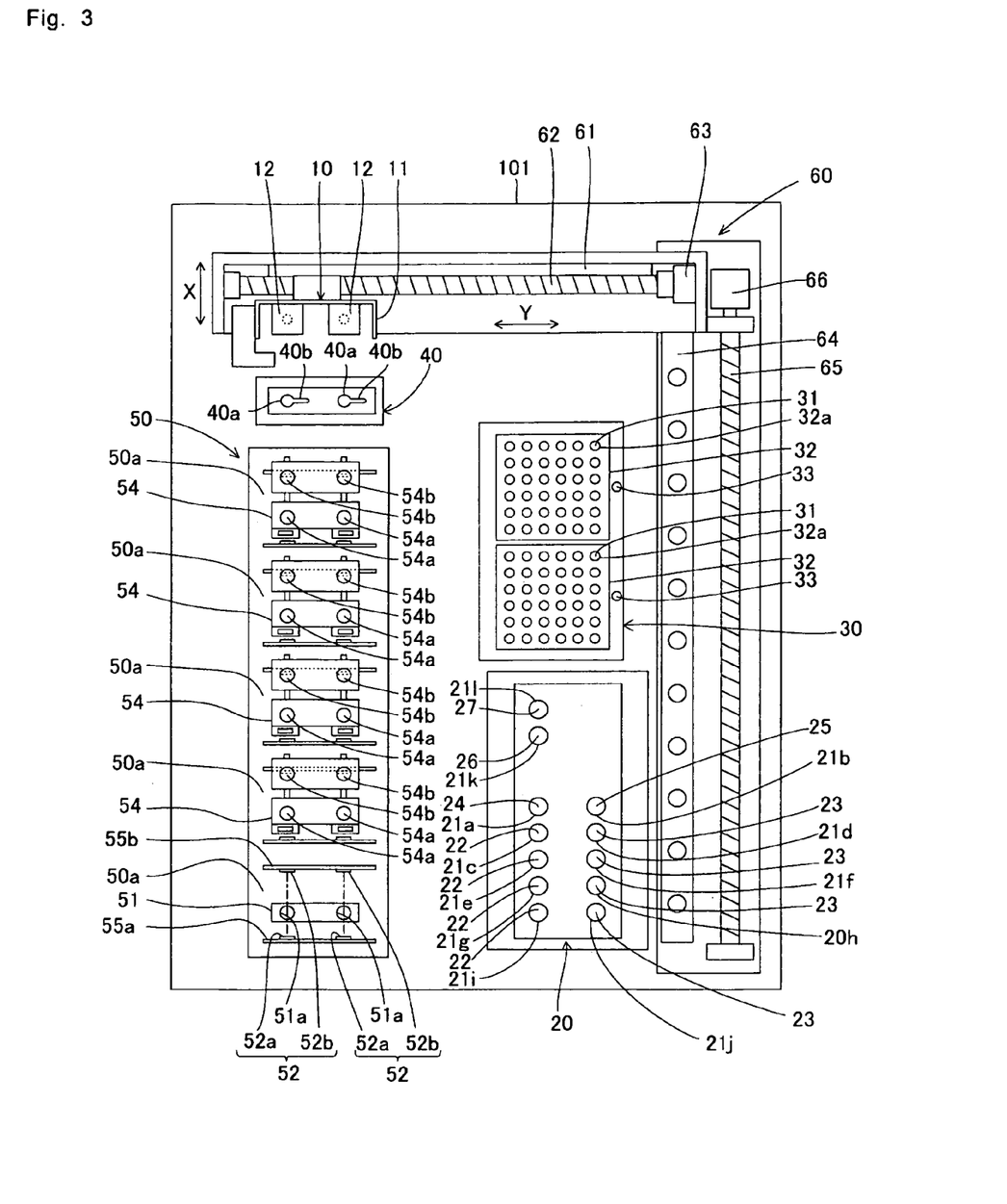
FIG. 3 is a schematic plan view of FIG. 2.

Further, the dispensing mechanism 10 includes, as shown in FIGS. 2 and 3, an arm portion 11 which is moved in X-axis direction and Y-axis direction (horizontal direction) by the transfer unit 60, and a double (two) syringe unit 12 each capable of moving independently in Z-axis direction (vertical direction) with regard to the arm portion 11.

Further, as shown in FIGS. 2 and 3, to the sample specimen setting unit 20 are provided, sequentially from the front of the apparatus, ten sample container setting holes 21a. through 21j, one enzyme reagent container setting hole 21k. and one primer reagent container setting hole 21l. Further, ten sample container setting holes 21a. through 21j. are provided being arranged in five lines and two rows. And, sample container setting holes 21c. and 21d, sample container setting holes 21e and 21f, sample container setting holes 21g. and 21h, sample container setting holes 21i. and 21j. are provided to, sequentially from the back of the apparatus, sample setting position 1, sample setting position 2, sample setting position 3, and sample setting position 4.

Besides, according to the present embodiment, to the sample container setting holes 21c, 21e, 21g. and 21i. at the left of the front, is set a sample container 22 in which solubilization extraction liquid (sample specimen), produced in advance by treatment (homogenization, filtering or the like) of a resected living tissue (lymph node), is accommodated, and to the sample container setting holes 21d, 21f, 21h. and 21j. at the right of the front, is set a sample container 23 in which each of dilution samples (ten-fold dilution) of abovementioned sample specimens are accommodated. Specifically, a dilution sample corresponding to a sample specimen accommodated in the sample container 22 which is to be set in the sample container setting hole 21c. is accommodated to a sample container 23 of the sample container setting hole 21d. Further, a dilution sample corresponding to a sample specimen accommodated in the sample container 22 which is to be set in the sample container setting hole 21e. is accommodated to a sample container 23 of the sample container setting hole 21f, a dilution sample corresponding to a sample specimen accommodated in the sample container 22 which is to be set in the sample container setting hole 21g. is accommodated to a sample container 23 of the sample container setting hole 21h, a dilution sample corresponding to a sample specimen accommodated in the sample container 22 which is to be set in the sample container setting hole 21i. is accommodated to a sample container 23 of the sample container setting hole 21j. In other words, two samples (sample specimen, dilution sample) are produced from one living tissue. In the meantime, in the present embodiment, unpurified samples (target nucleic acid is not purified) are used as the sample specimen and the dilution sample.

Further, a container 24, in which a positive control for confirming that a gene to be amplified is amplified normally is accommodated, is placed to the sample container setting hole 21a. and at the same time, a container 25, in which a negative control for confirming that a gene not to be amplified is not amplified normally is accommodated, is set in a sample container setting hole 21b.

To an enzyme reagent container setting hole 21k. and to a primer reagent container setting hole 21l are set an enzyme reagent container 26 accommodating DNA polymerase and reverse transfer enzyme as an enzyme reagent and a primer reagent container 27 accommodating primer reagent of CK19. are set, respectively.

Further, as shown in FIG. 3, two racks 32 each having an accommodation hole 32a. capable of accommodating 36 pieces of pipette chips 31 are inserted detachably into the chip setting unit 30. Two removal buttons 33 are provided to the chip setting unit 30. By pressing the removal button 33, racks 32 are put into removable state.

As shown in FIG. 3, two chip disposal holes 40a. for disposal of used pipette chip 31 are provided to the chip disposal unit 40. Besides, a groove portion 40b. having width narrower than the chip disposal hole 40a. is provided to be continued to the chip disposal hole 40a.

Further, as shown in FIGS. 2 and 3, each of reaction detection blocks 50a. of the reaction detection unit 50 comprises a reaction unit 51, two turbidity detection units 52 and a cover closing mechanism 53 (see FIG. 3). As shown in FIG. 3, to the reaction unit 51 provided to each of reaction detection blocks 50a. is provided two detection cell setting holes 51a. for setting a detection cell 54. Each of the reaction detection blocks 50a is disposed to, sequentially from the back of the apparatus, cell setting position 1, cell setting position 2, cell setting position 3, cell setting position 4, and cell setting position 5.

Further, the turbidity detection units 52 comprise, as shown in FIG. 3, an LED light source 52a. comprising blue LED having 465. nm wavelength which is mounted to a substrate 55a. disposed at one side face of the reaction unit 51, and a photodiode light receiving unit 52b. which is mounted to a substrate 55b. disposed to other side face of the reaction unit 51. One set of turbidity detection units 52 each comprising one LED light source 52a. and one photodiode light receiving unit 52b. is disposed by two sets to each of reaction detection blocks 50a. Therefore, the turbidity detection unit 52 comprising a total ten sets of LED light sources 52a. and photodiode light receiving units 52b. is disposed to five reaction detection blocks 50a. The LED light source 52a. and the photodiode light receiving unit 52b. corresponding thereto are disposed so that a light approximately 1. mm in the diameter is irradiated from the LED light source 52a. to lower part of the detection cell 54 and this light could be received by the photodiode light receiving unit 52b. With the use of intensity of the light received by the photodiode light receiving unit 52b, presence or absence of the detection cell 54 can be detected and turbidity of the liquid accommodated inside of the cell unit 54a. of the detection cell 54 can be monitored by a display unit 102c. of the personal computer 102, which will be described later. Specifically, when the detection cell 54 is set in the detection cell setting hole 51a, since the detection cell 54 is being disposed between the LED light source 52a. and photodiode light receiving unit 52b, a light received by the photodiode light receiving unit 52b. becomes weaker than the case where the detection cell 54 is not set. It is now possible to detect that the detection cell 54 is being set.

Further, the detection cell 54 has two cell units 54a. for accommodating the sample specimen and the dilution sample, and two cover units 54b. for covering two cell units 54a.

Further, the transfer unit 60 includes, as shown in FIGS. 2 and 3, a direct operation guide 61 and ball screw 62 for transferring the dispensing mechanism 10 in Y-axis direction, a stepping motor 63 for driving the ball screw 62, a direct operation guide 64 and a ball screw 65 for transferring the dispensing mechanism 10 in X-axis direction, a stepping motor 66 for driving the ball screw 65. Meanwhile, transfers of the dispensing mechanism 10 in X-axis direction and in Y-axis direction are performed by turning the ball screw 62 and 65 by the stepping motor 63 and 66, respectively.

The personal computer 102 includes, as shown in FIG. 1, a keyboard 102a. and a mouse 102b. serving as the input device, the display unit 102c. comprising a monitor, and a CPU 102d. for analyzing measurement results of the sample specimen and the dilution sample. Next, referring to FIG. 1 and FIGS. 4 to 8, details of screen layout of the display unit 102c. of the personal computer 102 will be explained.

The display unit 102c. is provided to display a screen (data browser screen) for displaying measurement results of the sample specimen being analyzed by the CPU 102d, a screen (workload list screen) for giving measurement instructions such as registration of sample ID using the keyboard 102a. and the mouse 102b, and a screen (analytical curve display screen) for displaying the analytical curve, or the like.

Figure 4:
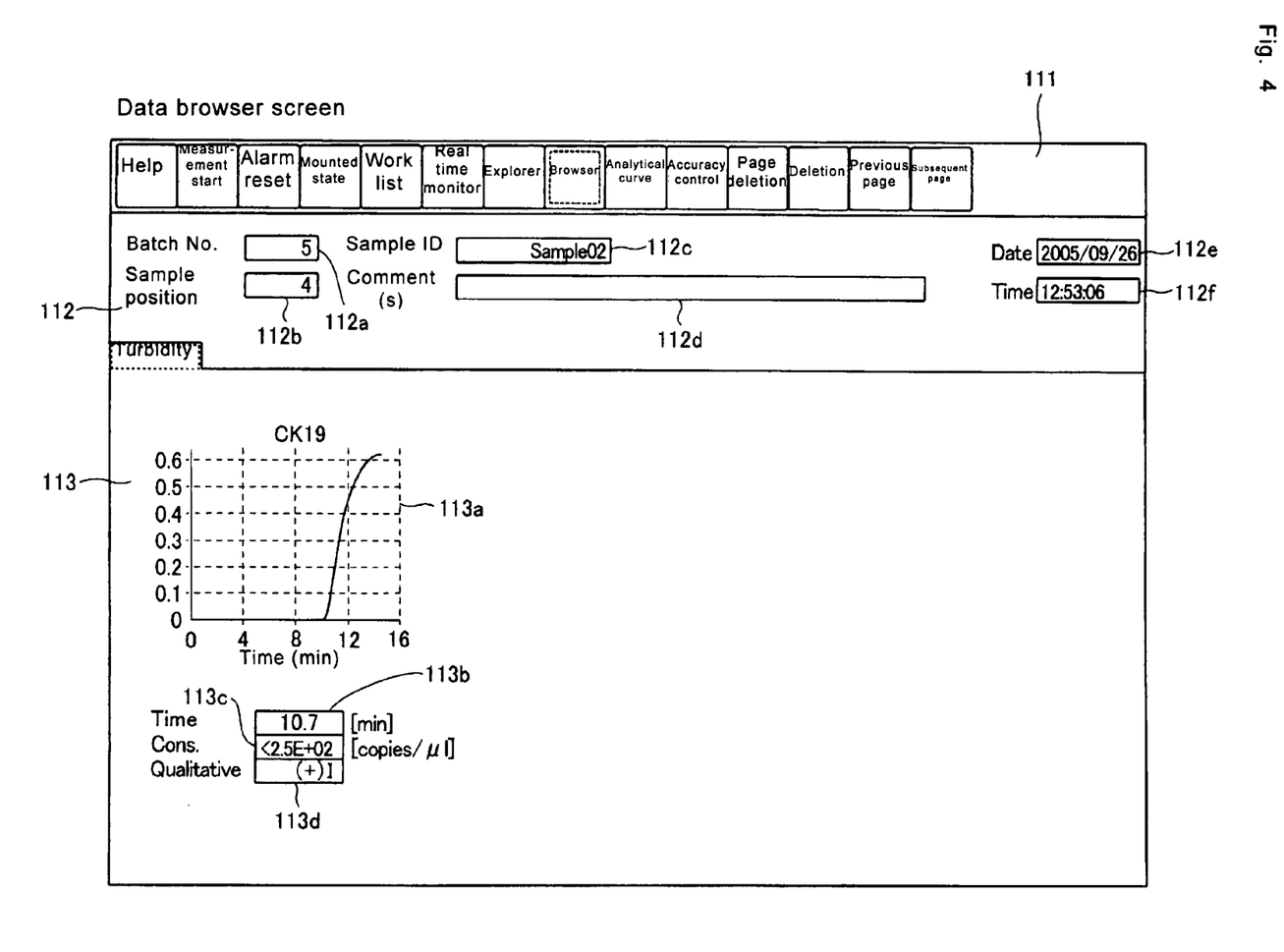
FIG. 4 is a drawing showing data browser screen displayed on the display unit of personal computer composing the gene amplification and analysis system by one embodiment shown in FIG. 1.

On the data browser screen, as shown in FIG. 4, a tool bar 111 which displays buttons for executing various functions such as help function, a sample information display unit 112 for displaying various information of the sample specimen, and a measurement results display unit 113 for indicating measurement results of the sample specimen which are displayed on the sample information display unit 112, are displayed.

Further, on the sample information display unit 112 are provided a batch number display column 112a, a sample position display column 112b, a sample ID display column 112c, a comment display column 112d, a measurement date display column 112e, and a measurement time display column 112f. The batch number display column 112a. shows what number of batch processing is taking place. Meanwhile, batch processing means that a plurality of sample specimens and dilution samples are processed collectively (in the present embodiment, a maximum of four sample specimens and a maximum of four dilution samples) In the batch number display column 112a, a numeral showing the number of times of batch processing executed after power supplying plus "1" is shown ("5" in the screen). In the sample position display column 112b, sample setting position where the sample specimen is being set is displayed ("4" in the screen). In the sample ID display column 112c. and comment display column 112d, comments for sample ID of the sample specimen entered in the workload list screen which will be described later ("Sample 02" on the screen) and for the sample specimen (dilution sample) (blank on the screen) are displayed, respectively. Further, in the measurement date display column 112e. and measurement time display column 112f, date of measurement of the sample specimen and the dilution sample ("2005/09/26" on the screen) and time ("12:53:06" on the screen) are displayed.

Further, on the measurement results display unit 113, graph 113a. showing relationship between turbidity of the sample specimen identified from above-mentioned batch number display column 112a. and sample position display column 112b. and time (min), amplification rising time display column 113b, concentration measurement display column 113c, and judgment result display column 113d. are provided. In the meantime, according to the present embodiment, measurement results of the dilution sample (graph, amplification rising time, concentration measurement and judgment results) are set so that users other than the administrator are not permitted to take a look. As a result, it is possible to remove such a chance that users may consider measurement result of the dilution sample as measurement result of the sample specimen.

Further, in the amplification rising time display column 113b, time corresponding to turbidity 0.1. on the vertical axis of the graph 113a. ("10.7" on the screen) is displayed.

Further, according to the present embodiment, in the concentration measurement display column 113c, concentration or range of concentration of the sample specimen calculated from the rising time (=10.7) (min) displayed on the amplification rising time display column 113b. ("<2.5E+02" on the screen) (copies/μl) is displayed. Specifically, concentration is calculated from amplification rising time (=10.7) based on the analytical curve (see FIG. 8) that is a linear function of amplification rising time and concentration prepared by a calibrator measured in advance. When the concentration is not less than $2.5 \times 10^2$. (copies/μl), concentration actually measured is displayed within the range of linearity assurance "2.5E+07. copies/μl", and when it is less than $2.5 \times 10^2$. (copies/μl), "<2.5E+02" is displayed. When the range of linearity assurance "2.5E+07. copies/μl" is exceeded, ">2.5E+07" is displayed.

Figure 5:
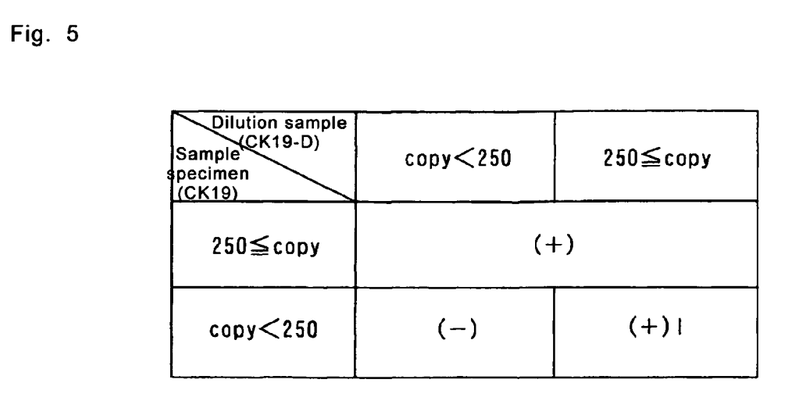
FIG. 5 is a drawing showing relationship between measurement results of sample specimen, measurement results of dilution sample, and existence or nonexistence of target gene.
Figure 6:
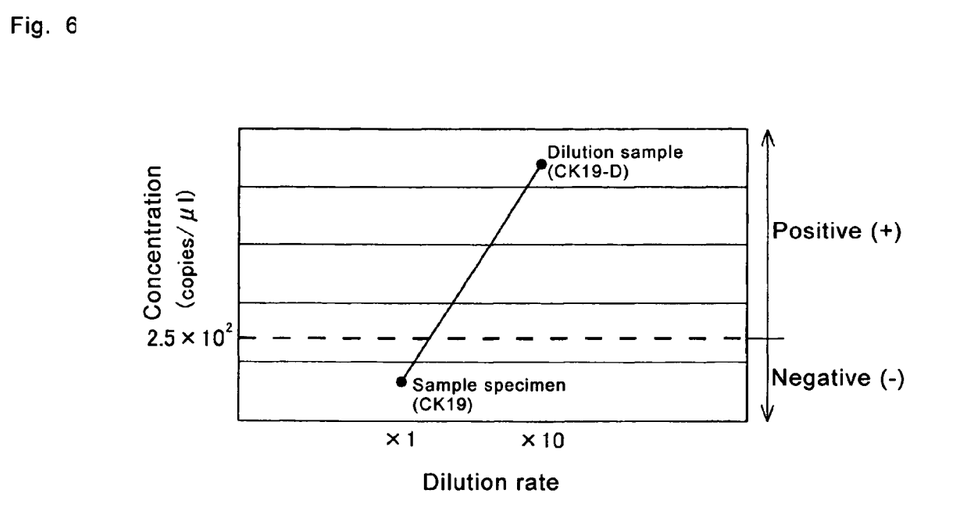
FIG. 6 is a graph showing relationship between dilution rate and concentration of sample specimen that caused amplification inhibition.

According to the present embodiment, the judgment result display column 113d. is provided to display the result of whether or not a target gene (mRNA) is present at a predetermined level or more in the sample specimen (positive "+", negative "−") based on the measurement result (concentration) of the sample specimen, and the measurement result (concentration) of dilution sample thereof. Further, the judgment result display column 113d. is provided to display information about amplification inhibition of target gene (mRNA) in the sample specimen together with the result of whether or not the target gene is present at the predetermined level or more as mentioned above. Specifically, as shown in FIG. 5, when measurement result of the sample specimen (CK19) is not less than $2.5 \times 10^2$ (copies/μl), "(+)" showing positive is displayed. When measurement result of a sample specimen is less than $2.5 \times 10^2$ (copies)/μl and measurement result of the dilution sample (CK19-D) of the sample specimen is less than $2.5 \times 10^2$. (copies)/μl, showing negative is displayed. When measurement result of the sample specimen (CK19) is less than $2.5 \times 10^2$. (copies)/μl and measurement result of the dilution sample (CK19-D) of the sample specimen is not less than $2.5 \times 10^2$. (copies)/μl, "(+) I" showing positive is displayed. Data browser screen shown in FIG. 4 shows an example of a case where measurement result of the sample specimen (CK19) is less than $2.5 \times 10^2$. (copies)/μl and measurement result of the dilution sample (CK19-D) of the sample specimen is not less than $2.5 \times 10^2$. (copies)/μl. This is such a case where, as shown in FIG. 6, although measurement result taken using a dilution sample (dilution of a sample specimen) is positive, measurement result taken using the sample specimen is negative. Meanwhile, "I" in "(+) I" that is shown when measurement result of a sample specimen is less than $2.5 \times 10^2$ (copies)/μl and measurement result of a dilution sample of the sample specimen is not less than $2.5 \times 10^2$. (copies)/μl, is a graph indicating that amplification inhibition occurred.

Figure 7:
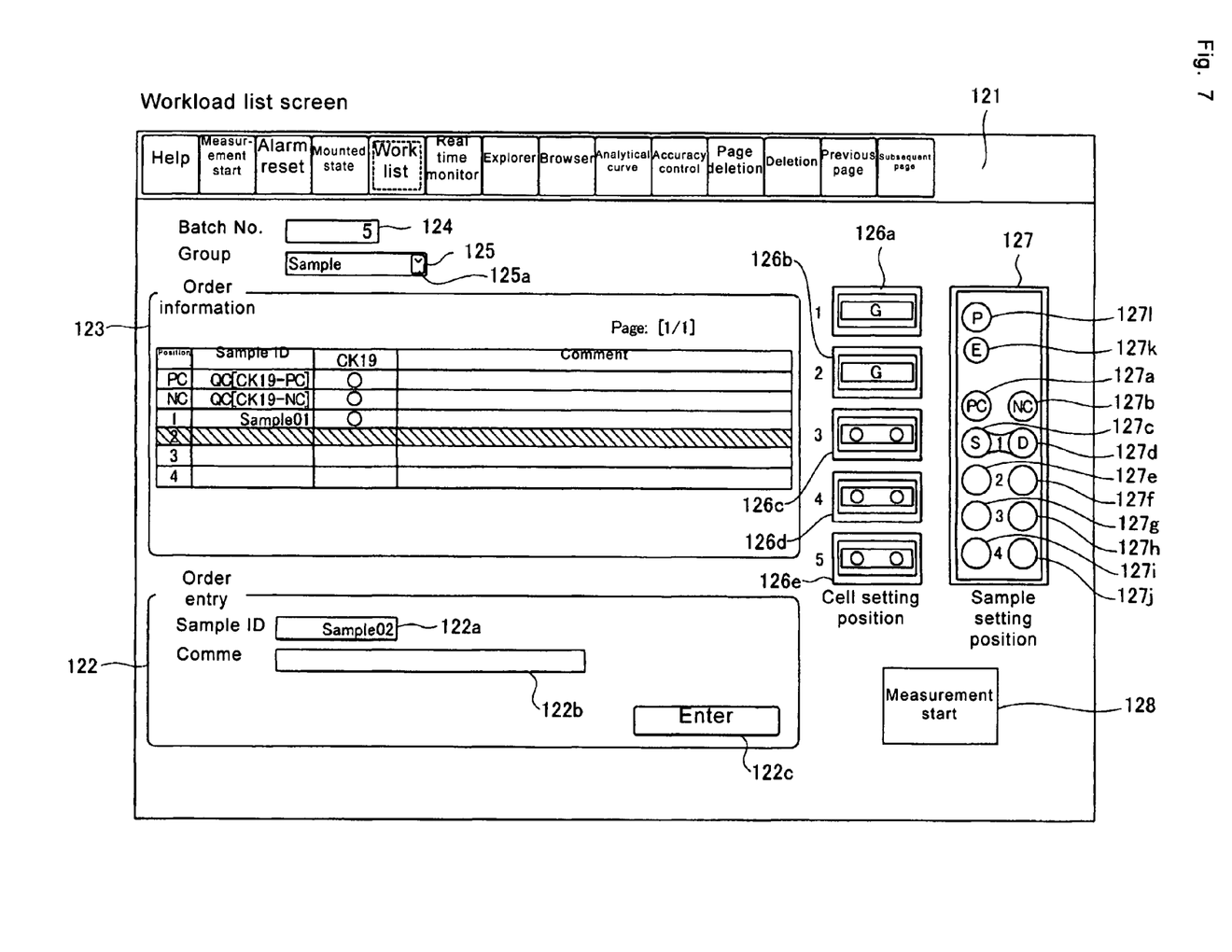
FIG. 7 is a drawing showing workload list screen displayed on the display unit of the personal computer composing the gene amplification and analysis system by one embodiment shown in FIG. 1.

On the workload list screen, as shown in FIG. 7, a tool bar 121 on which buttons for executing various functions such as printing function are displayed, an order entry unit 122 for entering measurement order (measurement indication), an order list display unit 123 for displaying status of measurement order registration, a batch number display column 124, a group selection column 125, cell setting position display units 126a to 126e, a sample setting position display unit 127, and a measurement start button 128 are displayed.

Further, the order entry unit 122 is provided to execute entry of measurement order for sample setting positions 1 to 4, and entry of measurement order for accuracy control sample (positive control, negative control) to be set in the sample container setting holes 21 and 21b. (see FIG. 3). To this order entry unit 122 are provided a sample ID entry column 122a, a comment entry column 122b. and an enter button 122c. Specifically, using the keyboard 102a, sample ID is entered to the sample ID entry column 122a. for sample specimen at sample setting positions 1 to 4, and accuracy control sample of sample container setting holes 21a. and 21b. As for the sample ID, ID corresponding to negative control or positive control as well as ID corresponding to the sample specimen is entered. As for ID of a sample, for example, "Sample 01~Sample 04" are used. As for sample ID of positive control, for example, "QC [CK19-PC]" is used. As for sample ID of negative control, for example, "QC [CK19-NC]" is used. When there is a comment(s), it is possible to enter the comment to the comment entry column 122b. of the order entry unit 122. When the enter button 122c is clicked by the mouse 102b, the sample ID and comment(s) being entered are reflected to the order list display unit 123.

The batch number display column 124 displays what number of batch processing is taking place in similar fashion as the batch number display column 112a. of the sample information display unit 112 of data browser screen (see FIG. 4). In the group selection column 125, a group is selected from a pulldown menu 125a. As for this group, for example, a group for measuring sample specimen, a group for measuring calibrator for obtaining an analytical curve, or the like is mentioned. The present embodiment shows an example of the case where the group for measuring a sample specimen (Sample) is selected. When this group (Sample) is selected, "O" is displayed at a place corresponding to CK19. on the order list display unit 123.

Further, cell setting position display units 126a. to 126e are provided to display set status of the detection cell 54 of each of reaction detection blocks 50a. of the reaction detection unit 50. As for set status of the detection cell 54, when use is scheduled and the detection cell 54 is set in the detection cell setting hole 51a, "G" (displayed in green) is displayed on the cell setting position display units 126a. and 126b, as shown in FIG. 7. When the detection cell 54 is not set in the detection cell setting hole 51a. although use is scheduled, "NG" (displayed in red) is displayed at a predetermined place of the cell setting position display units 126a. to 126e. When setting of the detection cell 54 to the detection cell setting hole 51a is not required since use is not scheduled, a pattern (displayed in grey) showing the reaction unit 51 in a state, that there is no need for setting the detection cell 54 at a predetermined position of the cell setting position display units 126a. to 126e, is displayed.

Further, the sample setting position display unit 127 is provided to display set status of the sample container 22 for accommodating a sample specimen of the sample specimen setting unit 20 of the gene amplification measuring apparatus 101, the sample container 23 for accommodating dilution sample, the container 24 for accommodating positive control, the container 25 for accommodating negative control, the enzyme reagent container 26, and the primer reagent container 27. The sample setting position display unit 127 has sample container display units 127a. to 127j. corresponding to ten sample container setting holes 21a. to 21j, an enzyme reagent container display unit 127k corresponding to the enzyme reagent container setting hole 21k, and a primer reagent container display unit 127l corresponding to the primer reagent container setting hole 21l. Alphabets ("PC" on the screen) corresponding to sample ID (QC "CK19-PC") displayed on the order list display unit 123 are displayed on the sample container display unit 127a. Besides, alphabets ("NC" on the screen) corresponding to sample ID (QC "CK19-NC") displayed on the order list display unit 123 are displayed on the sample container display unit 127b.

Further, an alphabet ("S" showing sample on the screen) corresponding to sample ID displayed on the order list display unit 123 is displayed on the sample container display units 127c, 127e, 127g. and 127i. An alphabet ("D" showing dilution on the screen) showing a dilution sample is displayed on sample container display units 127d, 127f, 127h. and 127j. On the enzyme reagent container display unit 127k. is displayed an alphabet ("E" on the screen) showing that the enzyme reagent container 26 is being set, and on the primer reagent container display unit 127l is displayed an alphabet ("P" on the screen) showing that the primer reagent container 27 is placed. In the present embodiment, a screen showing that entry of measurement order for sample setting position 1 has been completed is shown.

Figure 8:
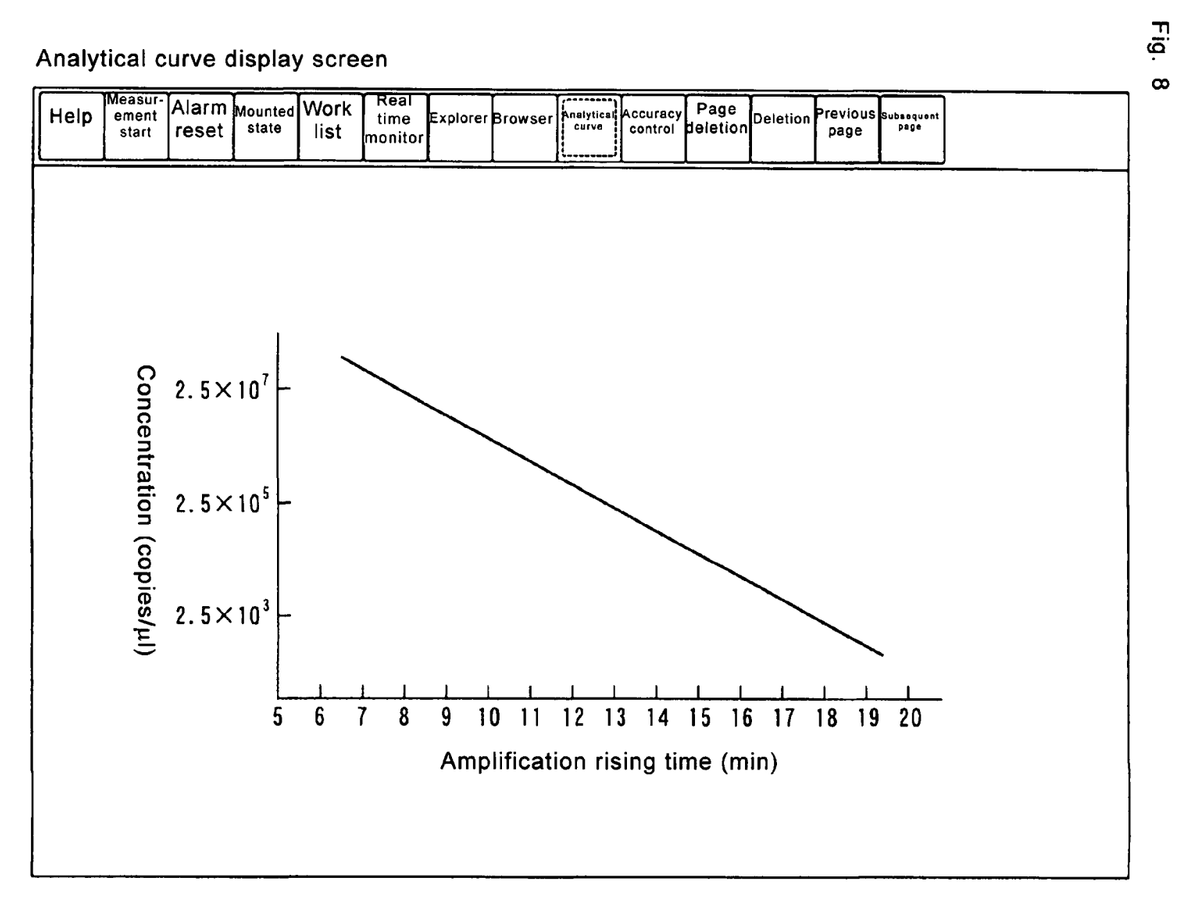
FIG. 8 is a drawing showing analytical curve display screen displayed on the display unit of the personal computer composing the gene amplification and analysis system by one embodiment shown in FIG. 1.

The analytical curve display screen is, as shown in FIG. 8, a screen for displaying an analytical curve prepared by measuring calibrator of three known concentrations ($2.5 \times 10^3$ (copies/µl), $2.5 \times 10^5$. (copies/µl), $2.5 \times 10^7$. (copies/µl)), and three concentration points plotted against calibrator rising amplification time are represented by a straight line approximated by linear expression.

Next, referring to FIGS. 1 to 4, FIGS. 7 and 8, operations of the gene amplification analysis system 1 according to the present embodiment will be explained. With the gene amplification analysis system 1 according to the present embodiment, as mentioned above, a target gene (mRNA) derived from a cancer which is present in a tissue resected at cancer operation is amplified using LAMP method, white turbidity due to magnesium pyrophosphate generated by amplification is measured to make judgment whether or not the target gene exists at the predetermined level or more. In the meantime, with LAMP method used in the present embodiment, although a treatment for extracting the target gene (mRNA) by treating the resected tissue is performed, no purification treatment is performed.

First, as shown in FIG. 2 and FIG. 3, the sample containers 22, in which is accommodated a solubilization extraction liquid (sample specimen) produced in advance by treatment (homogenization, filtering or the like) of the resected tissue, are set in the sample container setting holes 21c, 21e, 21g. and 21i. The sample containers 23 accommodating the dilution samples in which sample specimen to be accommodated in the sample container 22 is diluted ten-fold, are set in the sample container setting holes 21d, 21f, 21h. and 21j. The container 24 in which positive control is accommodated and the container 25 in which negative control is accommodated are set in the sample container setting hole 21a. and 21b, respectively (see FIG. 3). The enzyme reagent container 26 in which enzyme reagent of CK19. is accommodated, and the primer reagent container 27 in which primer reagent of CK19. is accommodated are set in the enzyme reagent container setting hole 21k. (see FIG. 3) and the primer reagent container setting hole 21l respectively. Further, two racks 32 each accommodating 36 pieces of disposable pipette chips 31 are mounted to the chip setting unit 30.

Before starting measurements, measurement instructions such as registration of sample ID are given on the screen of the display unit 102c. of the personal computer 102 (workload list screen (see FIG. 7) ) using the keyboard 102a. and the mouse 102b. of the personal computer 102 shown in FIG. 1.

The user then clicks, using the mouse 102b. (see FIG. 1), the measurement start button 128 on the workload list screen shown in FIG. 7. With this manipulation, measurement operations of the gene amplification measuring apparatus 101 are started.

When operations of the gene amplification measuring apparatus 101 are started, first, the arm portion 11 of the dispensing mechanism 10 is moved from an initial position to the chip setting unit 30 by the transfer unit 60 shown in FIG. 2, and then, at the chip setting unit 30, two syringe units 12 of the dispensing mechanism 10 are moved downwardly. By these operations, a front edge of nozzle part of each of two syringe units 12 is press fit into an upper opening of each of the two pipette chips 31 and therefore, the pipette chip 31 is automatically mounted to the front edge of nozzle part of each of two syringe units 12. After two syringe units 12 are moved upwardly, the arm portion 11 of the dispensing mechanism 10 is moved in X-axis direction towards upper part of the primer reagent container 27 in which primer reagent of CK19. is accommodated. After one syringe unit 12 located at upper part of the primer reagent container 27 is moved downwardly and primer reagent is sucked, other syringe unit 12 is then moved upwardly. After that, the arm portion 11 of the dispensing mechanism 10 is moved in Y-axis direction by the transfer unit 60 so that other syringe unit 12 may be positioned at upper part of the same primer reagent container 27. After other syringe unit 12 is moved downwardly and primer reagent is sucked from the same primer reagent container 27, the other syringe unit 12 is moved upwardly. In this way, primer reagent of CK19. in the primer reagent container 27 is sucked by two pipette chips 31 mounted to the syringe unit 12.

After the primer reagent is sucked and after two syringe units 12 are moved upwardly, the arm portion 11 of the dispensing mechanism 10 is moved by the transfer unit 60 above reaction detection block 50a. which is positioned at the cell setting position 1 that is the deepest (back of apparatus front). When two syringe units 12 are moved downwardly at the reaction detection block 50a. which is located at the deepest, two pipette chips 31 mounted to two syringe units 12 are inserted into two cell units 54a. of the detection cell 54, respectively. Following this, using the syringe unit 12, the primer reagent of CK19. is discharged to two cell units 54a, respectively.

After primer reagent is discharged and then two syringe units 12 are moved upwardly, the arm portion 11 of the dispensing mechanism 10 is moved by the transfer unit 60 in X-axis direction towards upper part of the chip disposal unit 40. Then, disposal of the pipette chip 31 is performed at the chip disposal unit 40. Specifically, after two syringe units 12 are moved downwardly, the pipette chip 31 is inserted into two chip disposal holes 40a. (see FIG. 3) of the chip disposal unit 40. In this state, when the arm portion 11 of the dispensing mechanism 10 is moved in Y-axis direction by the transfer unit 60, the pipette chip 31 is moved under the groove portion 40b. When two syringe units 12 are moved upwardly, flange portion on upper plane of the pipette chip 31 abuts lower plane at both sides of the groove portion 40b, thereby receiving a downward force from the lower plane, and therefore, the pipette chip 31 is automatically disengaged from nozzle part of each of two syringe units 12. By these operations, the pipette chip 31 is discarded to the chip disposal unit 40.

Next, the arm portion 11 of the dispensing mechanism 10 is moved again by the transfer unit 60 to the chip setting unit 30. Following this, at the chip setting unit 30, two new pipette chips 31 are automatically mounted to the front edge of the nozzle part of each of two syringe units 12 by the same operations as mentioned above. The arm portion 11 of the dispensing mechanism 10 is moved in X-axis direction towards upper part of the enzyme reagent container 26 in which is accommodated enzyme reagent of CK19. After one syringe unit 12 located at upper part of the enzyme reagent container 26 is moved downwardly and enzyme reagent is being sucked, the one syringe unit 12 is moved upwardly. Following this, the arm portion 11 of the dispensing mechanism 10 is moved in Y-axis direction by the transfer unit 60 so that other syringe unit 12 may be positioned at upper part of the same enzyme reagent container 26. After other syringe unit 12 is moved downwardly and enzyme reagent is being sucked from the same enzyme reagent container 26, the other syringe unit 12 is moved upwardly. In this way, enzyme reagents in the enzyme reagent container 26 are sucked by two pipette chips 31 mounted to the syringe unit 12.

After the arm portion 11 of the dispensing mechanism 10 is moved to upper part of the reaction detection block 50a located at the deepest by the transfer unit 60, the enzyme reagent of CK19. is discharged to two cell units 54a. of the detection cell 54. After the enzyme reagent is discharged, and after the arm portion 11 of the dispensing mechanism 10 is moved above the chip disposal unit 40 by the transfer unit 60, disposal of the pipette chip 31 is performed.

Next, the arm portion 11 of the dispensing mechanism 10 is moved again by the transfer unit 60 to the chip setting unit 30, two new pipette chips 31 are automatically mounted to the front edge of the nozzle part of each of two syringe units 12. The arm portion 11 of the dispensing mechanism 10 is moved in X-axis direction towards upper part of the sample container 22 and sample container 23 in which are accommodated the sample specimen and the dilution sample being set to the sample specimen setting unit 20, and after that, the sample specimen and the dilution sample in the sample containers 22 and 23 are sucked at once by the same suction operations of primer reagent and enzyme reagent as mentioned above. After that, the arm portion 11 of the dispensing mechanism 10 is moved above the reaction detection block 50a. located at the deepest by the transfer unit 60, and then two syringe units 12 are moved downwardly, and the sample specimen and the dilution sample are discharged to two cell units 54a. of the detection cell 54, respectively. Meanwhile, when dispensing primer reagent, enzyme reagent and sample specimen (dilution sample), temperature of liquid in the detection cell 54 is held at approximately 20° C. Following this, the arm portion 11 of the dispensing mechanism 10 is moved above the chip disposal unit 40 by the transfer unit 60, and then disposal of the pipette chip 31 is performed.

After primer reagent, enzyme reagent, sample specimen and the dilution sample are discharged into above-mentioned cell unit 54a, cover closing operation of the cover unit 54b. of the detection cell 54 is performed. After cover closing operation is completed, temperature of liquid in the detection cell 54 is heated from approximately 20° C. to approximately 65°. C. to allow amplification of target gene (mRNA) by LAMP (gene amplification) reaction. Then, white turbidity due to magnesium pyrophosphate generated by amplification is detected by turbidimetry. Specifically, detection of turbidity is carried out by detecting (monitoring) turbidity in the detection cell 54 at amplification reaction using LED light source 52a. and photodiode light receiving unit 52b. shown in FIG. 3.

Turbidity data (first measurement results) of the sample specimen and turbidity data (second measurement results) of the dilution sample are transmitted from the gene amplification measuring apparatus 101 to the personal computer 102 in real time. Based on the first measurement results and second measurement results received, the CPU 102d. of the personal computer 102 judges whether or not gene amplification inhibition is caused.

Figure 10:
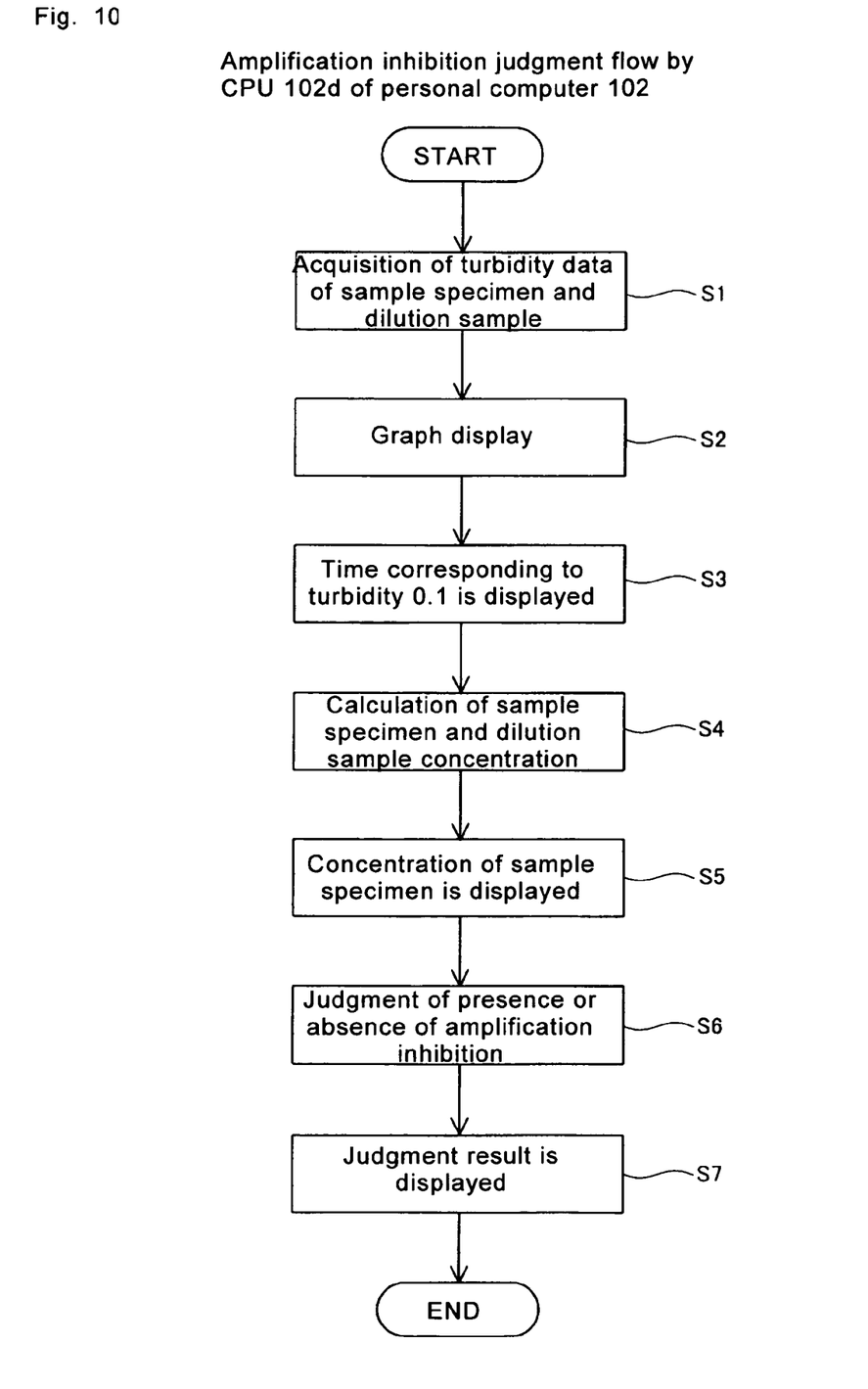
FIG. 10 is a flowchart showing amplification inhibition judgment flow of CPU of the personal computer of the gene amplification and analysis system by one embodiment shown in FIG. 1.

Now, referring to FIG. 10, amplification inhibition judgment flow of the CPU 102d. of the personal computer 102 will be explained. First, in step S1, the CPU 102d. receives from the gene amplification measuring apparatus 101 turbidity data of the sample specimen and the dilution sample, respectively and acquires them. Subsequently, in step 2, based on the turbidity data of the sample specimen and the dilution sample, the CPU 102d. displays a graph 113a. as shown in FIG. 4 showing relationship between reaction time (min) and turbidity on data browser screen of the display unit 102c. The graph 113a. shown in FIG. 4 is a graph that shows relationship between reaction time (min) of the sample specimen and turbidity. Step S1 to step S2, in which turbidity data are acquired and the graph 113a is displayed, are carried out in real time and it is designed so that display of the graph 113a. is renewed whenever turbidity data is received. When reaction time reaches 16. min, acquisition of data and display of graph 113a. are completed.

Next, in step S3, the CPU 102d. displays rising time "10.7 (min)" of the sample specimen corresponding to turbidity 0.1 in the graph 113a. in the amplification rising time display column 113b. In step S4, the CPU 102d. calculates nucleic acid concentrations of the sample specimen and the dilution sample from rising time of each of the sample specimen and the dilution sample and from the analytical curve shown in FIG. 8. In step S5, the CPU 102d. displays nucleic acid concentration or range of nucleic acid concentration of the sample specimen ("<2.5E+02" on the screen) on the concentration measurement display column 113c. Next, in step S6, the CPU 102d. judges presence or absence of amplification inhibition based on nucleic acid concentration of each of the sample specimen and the dilution sample. Specifically, it is judged that amplification inhibition is caused when nucleic acid concentration of a sample specimen is less than $2.5 \times 10^2$. (copies/µl) and nucleic acid concentration of the sample specimen is not less than $2.5 \times 10^2$ (copies/µl). Cases other than this are judged that no amplification inhibition is caused. Then, in step S7, the CPU 102d. displays flag "I" indicating amplification inhibition occurrence in the judgment result display column 113d. In the meantime, although nucleic acid concentration in the sample is calculated from rising time of the sample corresponding to turbidity 0.1. and the analytical curve shown in FIG. 8 after reaction time reached 16. min, nucleic acid concentration in the sample may be calculated from rising time of the sample corresponding to turbidity 0.1. and the analytical curve shown in FIG. 8 at the point when turbidity reaches 0.1. before reaction time reaches 16. min. If this is the case, step S1 to step S2, and step S3 through step S7 are subjected to parallel processing.

As mentioned above, detection of a target gene (mRNA) is carried out at the reaction detection block 50a. located at the deepest and at the same time, detection result is displayed on the display unit 102c. Further, for reaction detection blocks 50a. at second to fourth from the back, the same target gene detection operations as observed at the reaction detection block 50a. at the cell setting position 1 are performed sequentially. And, at the reaction detection block 50a. located at the cell setting position 5 located at fifth from the back, in similar fashion as target gene detection operation at the reaction detection block 50a. at the cell setting position 1 as mentioned above, the positive control in the container 24 being set in the sample container setting hole 21a. of the sample specimen setting unit 20 and the negative control in the container 25 being set in the sample container setting hole 21b are measured, and judgment is made whether or not detection results at the reaction detection block 50a. at cell setting positions 1 to 4 are correct. By these operations, one batch processing, in which four sample specimens (including four dilution samples) are processed collectively, is completed. In this way, operations of the gene amplification and analysis system 1 is completed by executing batch processing as many as the predetermined times.

According to the present embodiment, as mentioned above, in some cases, it is possible to confirm amplification of a target gene (mRNA), that was once judged to be negative by measurement result by the sample specimen, to be positive from measurement result of a dilution sample, as shown by the graph in FIG. 6, by acquiring measurement result (concentration) obtained by a dilution sample of primer and nucleic acid amplification enzyme and sample specimen, in addition to measurement result (concentration) obtained by primer and nucleic acid amplification enzyme and sample specimen. This is attributable to that inhibition substances, which adhered to a target gene and nucleic acid amplification enzyme at the time of measurement by sample specimen and inhibited amplification of the target gene, are liberated in the dilution sample at the time of measurement of the dilution sample. In this case, it is possible to judge that amplification inhibition of the target gene was caused at the time of measurement of the sample specimen from measurement result by the sample specimen with which amplification of the target gene was not confirmed and from measurement result by the dilution sample with which amplification of the target gene was confirmed. As a result, it is possible to acquire an accurate measurement result in which presence or absence of occurrence of amplification inhibition is taken into account, from measurement result by the sample specimen and measurement result by the dilution sample.

Further, in the present embodiment, by providing the display unit 102c. for displaying information relating to amplification inhibition of target gene (mRNA), it is possible for the user to confirm information concerning amplification inhibition (flag "I") acquired based on measurement result (concentration) by sample specimen and measurement result (concentration) by dilution sample.

Further, in the present embodiment, by causing the CPU 102d. of the personal computer 102 to judge whether or not a target gene (mRNA) is present at the predetermined level or more (positive "+", negative "−") based on measurement result by the dilution sample and to output judgment result (flag "I") of amplification inhibition of presence of the target gene not less than the predetermined level by the CPU 102d, together with judgment result of amplification inhibition (flag "I"), to the display unit 102c, it is possible to judge whether or not a target gene is present at the predetermined level or more with measurement result using dilution sample, without being affected by amplification inhibition, even a case where amplification inhibition is caused at the time of measurement of sample specimen, and therefore, it is possible to judge accurately whether or not a target gene is present at the predetermined level or more. Further, users can confirm not only presence or absence of amplification inhibition but also whether or not a target gene is present at the predetermined level or more by outputting judgment result of whether or not a target gene is present at the predetermined level or more, together with judgment result of amplification inhibition to the display unit 102c Further, in the present embodiment, it is possible to confirm amplification of a target gene (mRNA), that could not be confirmed by measurement by sample specimen, from measurement result by dilution sample, by using unpurified samples as the sample specimen and the dilution sample, and by acquiring measurement result measured by using the dilution sample in addition to measurement result by the sample specimen, even if a large amount of inhibitory substances are contained in the sample specimen and the dilution sample. As a result, it is possible to acquire accurate measurement result promptly even if unpurified sample specimen and the dilution sample, which do not require time for purifying target gene (mRNA) from sample specimen and the dilution sample, are used.

It should be understood that embodiments disclosed herein are exemplifications in all respects and do not constitute a limit. The scope of the present invention is defined by the appended claims, but by not descriptions of the embodiments described above, and all modifications within the appended claims and equivalents are considered to be included within the scope of the present invention.

For example, in the above-mentioned embodiment, although a case where the present invention is applied to a gene amplification and analysis system comprising a gene amplification measuring apparatus and a personal computer, the present invention is not limited thereto, and the gene amplification measuring apparatus may be used alone or the gene amplification measuring apparatus may be configured to equip functions of the personal computer.

Further, in the above-mentioned embodiment, although such a case is exemplified where flag "I" indicating occurrence of amplification inhibition is displayed when measurement result (concentration) of sample specimen (CK19) is less than $2.5 \times 10^2$. (copies/µl) and at the same time, measurement result (concentration) of dilution sample of the sample specimen (CK19-D) is not less than $2.5 \times 10^2$. (copies/µl), the present invention is not limited thereto, and the flag indicating occurrence of amplification inhibition may be displayed when measurement result of the dilution sample is greater than measurement result of the sample specimen by comparing measurement result (concentration) of the sample specimen to measurement result (concentration) of dilution sample of the sample specimen.

Figure 9:
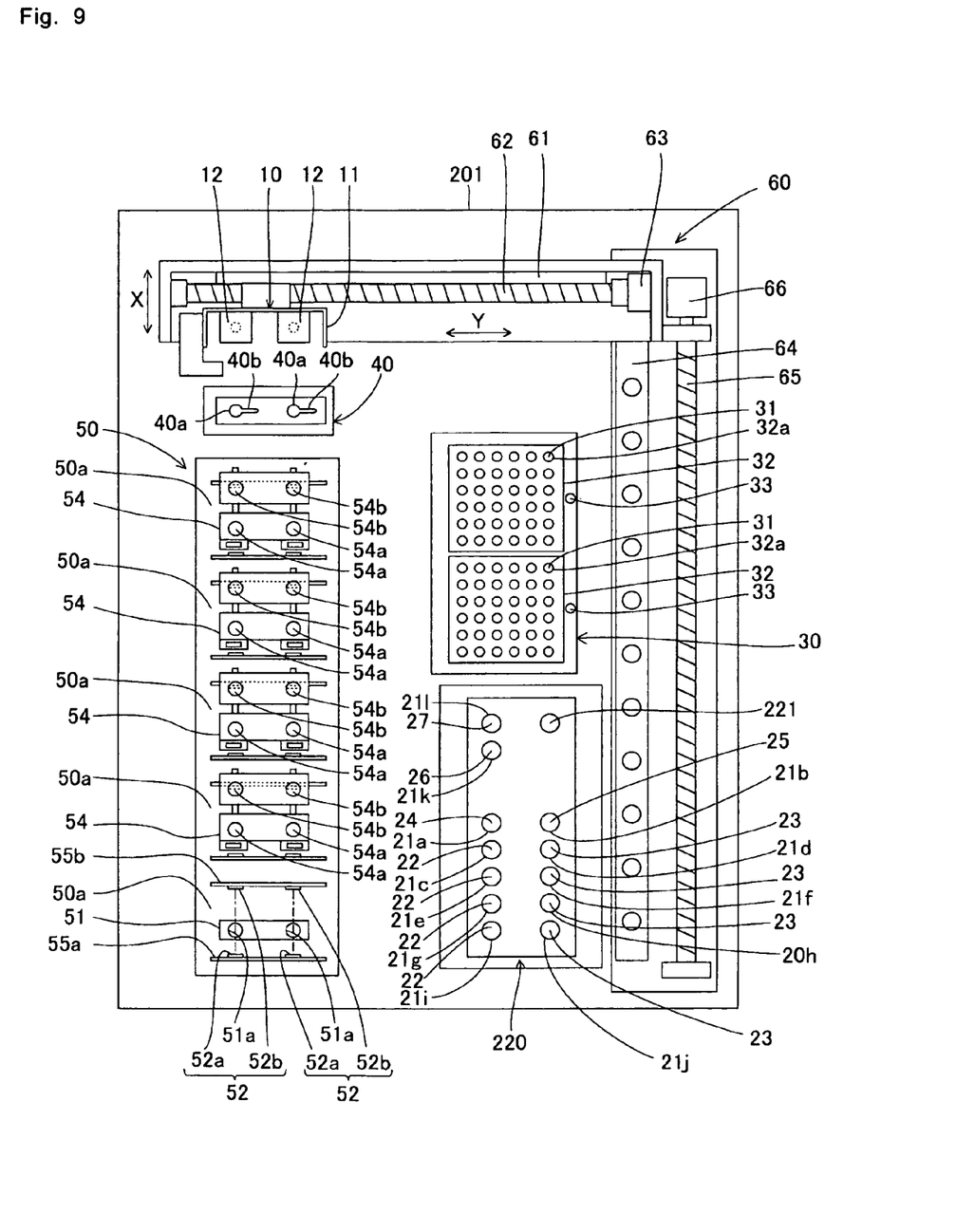
FIG. 9 is a schematic plan view showing variation of the gene amplification measuring apparatus of the gene amplification and analysis system by one embodiment shown in FIG. 1.

Further, in above-mentioned embodiment, although an example where a sample container accommodating the sample specimen and a dilution sample thereof is placed in the sample container setting hole of the sample specimen setting unit, the present invention is not limited thereto, and such an alternative may be made where as the gene amplification measuring apparatus 201 according to the variant of the present embodiment shown in FIG. 9, the dilution unit 221 for mounting a container accommodating dilution liquid is provided to the sample specimen setting unit 220, the dilution liquid is dispensed from the dilution unit 221 to one cell unit 54b. of the detection cell by the dispensing mechanism 10, and the dilution sample is produced automatically in the gene amplification measuring apparatus 201. In this case, it is preferable that, when measurement result of a sample specimen is not less than $2.5 \times 10^2$. (copies/µl), a dilution sample is not produced; and when measurement result of the sample specimen is less than $2.5 \times 10^2$. (copies/µl), the dilution sample is produced. With this consideration, when measurement result of a sample specimen is not less than $2.5 \times 10^2$. (copies/µl), it is apparent that judgment result is positive "(+)" and therefore, it is possible to suppress waste of dilution liquid required for preparation of dilution sample.

Further, in the above-mentioned embodiment, although it is judged that nucleic acid amplification product (target nucleic acid concentration) of dilution sample of sample specimen has amplification inhibition of target nucleic acid concentration, when nucleic acid amplification product (target nucleic acid concentration) of sample specimen is abundant, it may be judged that nucleic acid amplification product (target nucleic acid concentration) of dilution sample of sample specimen has amplification inhibition of target nucleic acid concentration when nucleic acid amplification product of dilution sample of sample specimen is more abundant than nucleic acid amplification product proportional to the dilution rate, even when nucleic acid amplification product (target nucleic acid concentration) of sample specimen is insufficient. For example, when nucleic acid amplification product of the sample specimen is $25 \times 10^2$. (copies/µl), nucleic acid amplification product of 10-fold dilution sample, which should be $2.5 \times 10^2$ (copies/µl), is $15 \times 10^2$. (copies/µl) and is not proportional to the dilution rate, it may be judged that there is amplification inhibition of target nucleic acid concentration.

Further, in the above-mentioned embodiment, although it is judged whether or not the target nucleic acid is present at a predetermined level or more by measuring magnesium pyrophosphate (nucleic acid amplification product) of the sample. In this case, it is preferable to judge whether or not the target nucleic acid is present at a predetermined level or more by measuring target nucleic acid amplification product of the sample.

Further, in above-mentioned embodiment, although the sample specimen, the enzyme reagent and the primer reagent of CK19. are dispensed from the sample container 22, the enzyme reagent container 26 and the primer reagent container 27 to one cell unit 54a. of the detection cell by the dispensing mechanism 10, and the dilution sample, the enzyme reagent and the primer reagent of CK19. are dispensed from the sample container 23, the enzyme reagent container 26 and the primer reagent container 27 to one cell unit 54b. of the detection cell by the dispensing mechanism 10. In this case, it is preferable that it is prepared a first sample from the sample specimen, the enzyme reagent and the primer reagent of CK19. and a second sample from the dilution sample, the enzyme reagent and the primer reagent of CK19, and it is dispensed the first sample and the second sample to the cell unit 54a. and 54b. of the detection cell by the dispensing mechanism 10, respectively.

What is claimed is:

1. A nucleic acid amplification apparatus for amplifying a target nucleic acid derived from a living organism, comprising:
   a sample setting part for setting a first container accommodating a first sample prepared from a living organism and a second container accommodating a second sample obtained by diluting the first sample;
   a reagent setting part for setting a third container accommodating a nucleic acid amplification enzyme and a fourth container accommodating a primer for a target nucleic acid in the living organism;
   a reaction container setting part for setting a first reaction container and a second reaction container;
   a dispensing unit for dispensing the first sample, the nucleic acid amplification enzyme and the primer to the first reaction container in order to prepare a first measurement sample that is not diluted, and dispensing the second sample, the nucleic acid amplification enzyme and the primer to the second reaction container in order to prepare a second measurement sample that is diluted;
   a measurement unit for amplifying the target nucleic acid in the first measurement sample in the first reaction container and the second measurement sample in the second reaction container, and measuring an amount of a product of the amplification of the target nucleic acid in each of the first measurement sample and second measurement sample, wherein the second measurement sample has a higher dilution ratio than that of the first measurement sample; and
   a hardware unit comprising:
   a controller configured to calculate a first measurement value from the first measurement sample without using any measurement value from a control sample, and a second measurement value from the second measurement sample without using any measurement value from a control sample, and judging that amplification inhibition of the target nucleic acid occurs when the second measurement value is larger than the first measurement value, or when the first measurement value and the second measurement value are not proportional to dilution ratios of the first measurement sample and the second measurement sample; and
   an output unit to output information from the controller indicating that the target nucleic acid in the living organism exceeds a predetermined amount, when:
   (1) the first measurement value is larger than a first threshold value, or
   (2) the first measurement value is smaller than the first threshold value, the second measurement value is larger than a second threshold value and amplification of the target nucleic acid is inhibited;
   wherein the information from the controller comprises at least one graph showing turbidity data of the first measurement sample and the second measurement sample, an amplification rising time display column, a concentration measurement display column, or a judgment result display column.

2. The nucleic acid amplification apparatus according to claim 1, wherein
   the output unit outputs information from the controller related to amplification inhibition.

3. The nucleic acid amplification apparatus according to claim 1, wherein
   the controller judges that the target nucleic acid in the living organism does not exceed the predetermined amount, when the first measurement value is smaller than the first threshold value and the second measurement value is smaller than the second threshold value.

4. The nucleic acid amplification apparatus according to claim 1, wherein the first threshold value is equal to the second threshold value.

5. A nucleic acid amplification apparatus for amplifying a target nucleic acid derived from a living organism, comprising:
   a sample setting part for setting a first container accommodating a sample prepared from a living organism;
   a dilution unit for setting a second container accommodating a dilution liquid;
   a reagent setting part for setting a third container accommodating a nucleic acid amplification enzyme and a fourth container accommodating a primer for a target nucleic acid in the living organism;
   a reaction container setting part for setting a first reaction container and a second reaction container;
   a dispensing unit for dispensing the sample, the nucleic acid amplification enzyme and the primer to the first reaction container in order to prepare a first measurement sample, and dispensing the sample, the dilution liquid, the nucleic acid amplification enzyme and the primer to the second reaction container in order to prepare a second measurement sample;

a measurement unit for amplifying the target nucleic acid in the first measurement sample in the first reaction container and the second measurement sample in the second reaction container, and measuring an amount of a product of the amplification of the target nucleic acid in each of the first measurement sample and second measurement sample, wherein the second measurement sample has a higher dilution ratio than that of the first measurement sample, and a hardware unit comprising:

a controller configured to calculate a first measurement value from the first measurement sample without using any measurement value from a control sample, and a second measurement value from the second measurement sample without using any measurement value from a control sample, and judging that amplification inhibition of the target nucleic acid occurs when the second measurement value is larger than the first measurement value, or when the first measurement value and the second measurement value are not proportional to dilution ratios of the first measurement sample and the second measurement sample; and an output unit to output information from the controller indicating that the target nucleic acid in the living organism exceeds a predetermined amount when: (1) the first measurement value is larger than a first threshold value, or (2) the first measurement value is smaller than the first threshold value, the second measurement value is larger than a second threshold value and amplification of the target nucleic acid is inhibited.

6. The nucleic acid amplification apparatus according to claim 5, wherein the sample in the first container is a pretreatment sample which is prepared from the living organism and a pretreatment liquid and contains solubilized nucleic acid.

7. The nucleic acid amplification apparatus according to claim 6, wherein the pretreatment sample is a sample in which nucleic acid is not purified.

8. The nucleic acid amplification apparatus according to claim 5, wherein the information comprises at least one graph showing turbidity data of the first measurement sample and the second measurement sample, an amplification rising time display column, a concentration measurement display column, and a judgment result display column.

9. The nucleic acid amplification apparatus according to claim 5, wherein the information comprises at least one graph showing turbidity data of the first measurement sample and the second measurement sample, an amplification rising time display column, a concentration measurement display column, or a judgment result display column.

10. A nucleic acid amplification apparatus for amplifying a target nucleic acid derived from living organism, comprising:

a sample setting part for setting a first container accommodating a first sample prepared from a living organism and a second container accommodating a second sample obtained by diluting the first sample;

a reagent setting part for setting a third container accommodating a nucleic acid amplification enzyme and a fourth container accommodating a primer for a target nucleic acid in the living organism;

a reaction container setting part for setting a first reaction container and a second reaction container;

a dispensing unit for dispensing the first sample, the nucleic acid amplification enzyme and the primer to the reaction container in order to prepare a first measurement sample that is not diluted, and dispensing the second sample, the nucleic acid amplification enzyme and the primer to the second reaction container in order to prepare a second measurement sample that is diluted;

a measurement unit for amplifying the target nucleic acid in the first measurement sample in the first reaction container and the second measurement sample in the second reaction container, and measuring an amount of a product of the amplification of the target nucleic acid in each of the first measurement sample and second measurement sample without using a control sample;

a controller configured to judge that a test result is positive when the first measurement value is larger than a predetermined threshold value, judge that a test result is negative when the first and second measurement values are not larger than the predetermined threshold value, and judge that a test result is positive and that amplification inhibition of the target nucleic acid occurred when the first measurement value is not larger than the predetermined threshold value and the second measurement value is larger than the predetermined threshold value; and an output unit to output information from the controller indicating a positive test result, a negative test result, or a positive test result and a flag showing the amplification inhibition.

11. The nucleic acid amplification apparatus according to claim 10, wherein the information comprises the positive test result when the first measurement value is larger than a predetermined threshold value.

12. The nucleic acid amplification apparatus according to claim 11, wherein the information comprises a graph showing turbidity data of the first measurement sample, an amplification rising time of the first measurement sample, or a concentration measurement of the first measurement sample.

13. The nucleic acid amplification apparatus according to claim 10, wherein the information comprises a graph showing turbidity data of the first measurement sample, an amplification rising time of the first measurement sample, and a concentration measurement of the first measurement sample.

14. The nucleic acid amplification apparatus according to claim 10, wherein the information comprises the negative test result when the first and second measurement values are not larger than the predetermined threshold value.

15. The nucleic acid amplification apparatus according to claim 10, wherein the information comprises the positive test result and the flag when the first measurement value is not larger than the predetermined threshold value and the second measurement value is larger than the predetermined threshold value.

16. The nucleic acid amplification apparatus according to claim 10, wherein the information comprises at least one graph showing turbidity data of the first measurement sample and the second measurement sample, an amplification rising time display column, a concentration measurement display column, or a judgment result display column.

17. The nucleic acid amplification apparatus according to claim 10, wherein the information comprises at least one graph showing turbidity data of the first measurement sample and the second measurement sample, an amplification rising time display column, a concentration measurement display column, and a judgment result display column.

18. The nucleic acid amplification apparatus according to claim 10, wherein the living organism is isolated from a cancer patient.

19. The nucleic acid amplification apparatus according to claim 18, wherein the living organism is a lymph node, the controller is configured to judge that a cancer metastasis is positive when the first measurement value is larger than a predetermined threshold value, judge that a cancer metastasis is negative when the first and second measurement values are not larger than the predetermined threshold value, and judge that a cancer metastasis is positive and amplification inhibition is occurred when the first measurement value is not larger than the predetermined threshold value and the second measurement value is larger than the predetermined threshold value.

* * * * *